United States Patent
Bartels et al.

(10) Patent No.: US 6,845,258 B2
(45) Date of Patent: Jan. 18, 2005

(54) MEDICAL EXAMINATION AND/OR TREATMENT INSTALLATION

(75) Inventors: Frank Bartels, Weidenberg (DE); Michael Heinold, Speichersdorf (DE); Rolf Reimann, Forchheim (DE)

(73) Assignee: Siemens Aktiengesellschaft, Münich (DE)

(*) Notice: Subject to any disclaimer, the term of this patent is extended or adjusted under 35 U.S.C. 154(b) by 280 days.

(21) Appl. No.: 10/096,238

(22) Filed: Mar. 12, 2002

(65) Prior Publication Data

US 2002/0165438 A1 Nov. 7, 2002

(30) Foreign Application Priority Data

Mar. 12, 2001 (DE) ........................................ 101 11 801

(51) Int. Cl.[7] ................................................. A61B 5/05
(52) U.S. Cl. ..................................................... 600/407
(58) Field of Search ..................... 5/600, 601; 600/410, 600/407, 411

(56) References Cited

U.S. PATENT DOCUMENTS

| | | | | |
|---|---|---|---|---|
| 4,011,609 A | * | 3/1977 | Bethlen | ........................ 5/600 |
| 4,715,591 A | * | 12/1987 | Dragmen, Sr. | ................. 5/601 |
| 4,795,142 A | | 1/1989 | Schaefer | |
| 5,615,430 A | * | 4/1997 | Nambu et al. | ................. 5/600 |
| 6,195,578 B1 | * | 2/2001 | Distler et al. | ............... 600/415 |
| 6,302,579 B1 | | 10/2001 | Meyer et al. | |
| 6,385,480 B1 | * | 5/2002 | Bachus et al. | ............. 600/411 |
| 2002/0104163 A1 | * | 8/2002 | Reimann | ....................... 5/601 |
| 2002/0129446 A1 | * | 9/2002 | Heinold et al. | ................ 5/601 |
| 2002/0174485 A1 | * | 11/2002 | Bartels | .......................... 5/601 |
| 2003/0126683 A1 | * | 7/2003 | Hand et al. | .................... 5/607 |
| 2004/0006821 A1 | * | 1/2004 | Hand et al. | .................... 5/607 |

FOREIGN PATENT DOCUMENTS

WO      WO 94/09738      5/1994

* cited by examiner

*Primary Examiner*—Ali Imam
(74) *Attorney, Agent, or Firm*—Schiff Hardin LLP

(57) ABSTRACT

A medical device installation has a number of medical and/or treatment devices of different of different types disposed at a common installation, and a medical facility has a number of medical treatment and/or examination devices respectively disposed at separate locations. In the installation or the facility, a number of patient support mechanisms are respectively individually, stationarily allocated to the medical devices. A patient bed is movable among and is respectively couplable to each of the patient support mechanisms. For this purpose, each of the patient support mechanisms has an identical coupling device for the bed.

11 Claims, 1 Drawing Sheet

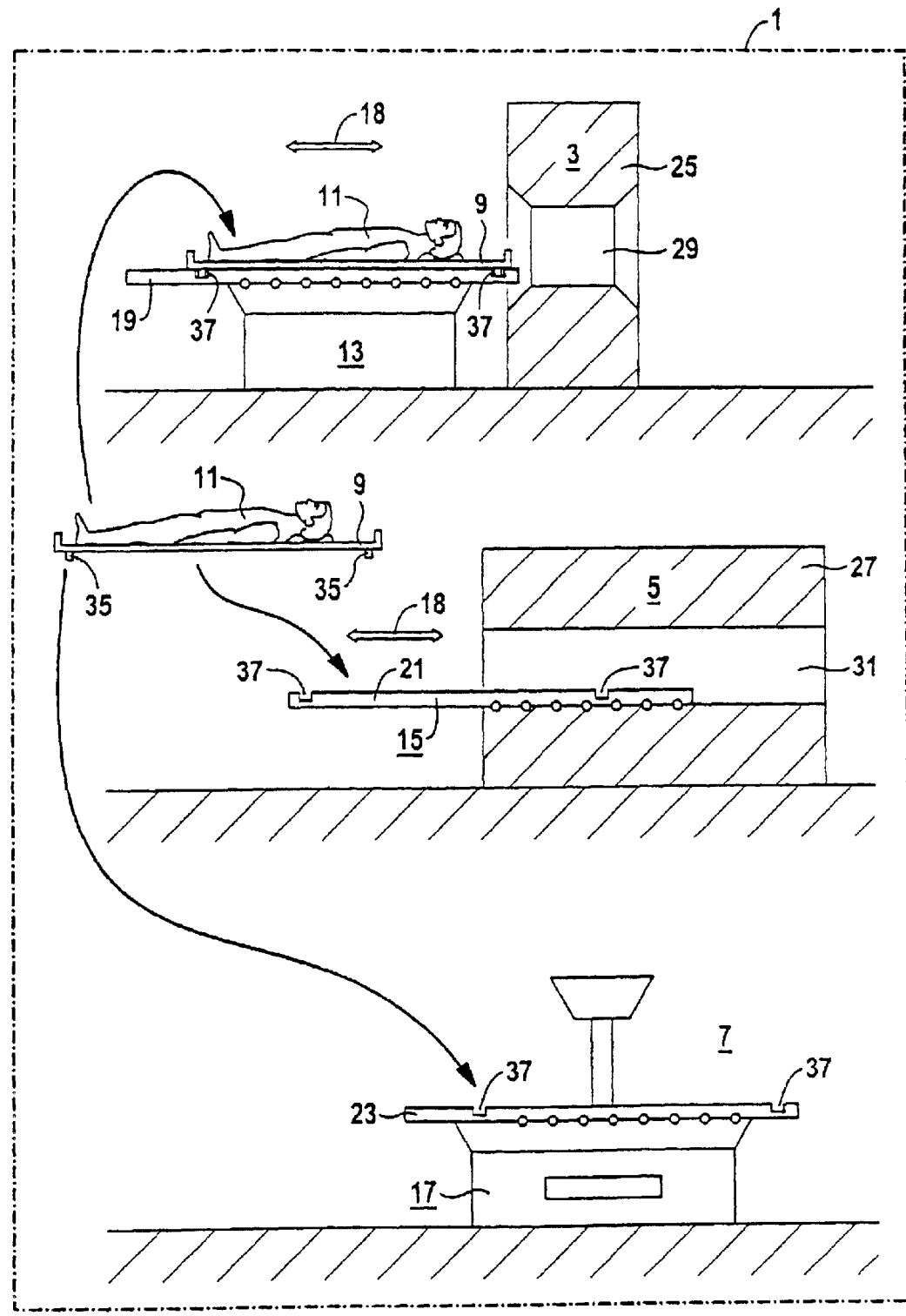

MEDICAL EXAMINATION AND/OR TREATMENT INSTALLATION

BACKGROUND OF THE INVENTION

1. Field of the Invention

The present invention is directed to an installation for the medical examination and/or treatment of a patient, of the type having a number of examination and/or treatment devices of different types each having a patient support mechanism, and with at least one patient bed.

The invention also is directed to a combination of a number of examination and/or treatment devices of different types for the medical examination and/or treatment of a patient, wherein a patient bearing mechanism is allocated to the examination and/or treatment devices.

2. Description of the Prior Art

Several different, medical examination devices and/or treatment devices are usually present in a large hospital. For a comprehensive medical examination and, possibly, treatment, a patient must frequently pass through a number of these examination and/or treatment devices. A number of re-bedding or repositioning procedures are needed for this purpose. For example, a patient delivered on a stretcher must be brought to a first examination room with a gurney and must be placed there on the patient bed of a patient support mechanism of the examination device that is located in this room. After the completion of this examination, the patient—again with the assistance of several aides—must be re-bedded onto the trolley. The patient is then moved into another examination room where a second examination device is located, where another re-bedding onto the patient bed of the second examination device is necessary. This procedure is time-consuming and strenuous for the medical personnel and for the patient, and must be repeated several times under certain circumstances if further examinations at further examination devices or a treatment at a treatment device are necessary. Moreover, severely injured patients, for example, trauma patients, can suffer further injury during a re-bedding procedure. Moreover, such a procedure requires time that is lost for urgent treatment or diagnostics.

SUMMARY OF THE INVENTION

An object of the present invention is to provide a medical examination and/or treatment installation wherein these disadvantages are avoided.

In an installation for medical examination and/or treatment of the type initially described, this object is inventively achieved by the patient bed being fashioned such that it can be coupled to each of the patient support mechanisms.

Because the patient bed can be coupled to each of the patient support mechanisms of the different examination and/or treatment devices, the patient to be examined can remain lying on the patient bed while passing through the various examination stations and/or, various of treatment modalities with a number of examination and/or treatment devices. A re-bedding is no longer required. The installation thus has a universal patient bed.

As used herein a "patient bed" is any and all means with which a patient can be borne in fashion including, for example, a bed board or a support plate.

The examination devices and/or treatment devices of the installation of the invention are of different types, i.e. they are based on different medical examination objectives or different treatment objectives, on different medical applications and/or different principles of physical action. Preferably, one of the examination devices is a magnetic resonance tomography apparatus, a computed tomography apparatus, or an angiography device, another is an x-ray transillumination system. One of the treatment devices can be, for example, a nuclear therapy device or a lithotripsy device.

The coupling of the patient bed ensues with a non-positive and/or positive lock.

The examination and/or treatment devices are connected to one another at least organizationally. Preferably, they are accommodated in a shared hospital, particularly in a common building.

In a preferred embodiment, each of the patient support mechanisms has a coupling device for releasably fastening the patient bed. Preferably the coupling devices are identical.

The patient support mechanisms, which are preferably rigidly or stationarily allocated to the respective examination and/or treatment devices, can in turn have a further patient bed that is allocated to them or is stationary and on which the universally couplable patient bed can in turn be coupled. This produces the advantage that each of the examination and/or treatment devices is also operational without the universally employable patient bed. The patient support mechanism itself, however, can also be implemented without a permanently allocated patient bed, for example as a pedestal or under-carriage.

Preferably, the universal patient bed cannot be upwardly removed in the coupled condition. It can also be secured against lateral dislocation. The patient bed thus does not merely lie loosely on the support mechanism in the coupled condition.

Particularly in the coupled condition, the patient bed can be introduced with the respective patient support mechanism into an examination or treatment region, particularly into an opening in a housing, of the respective examination and/or treatment device. To this end, the patient support mechanism can have a movable carriage to which the patient bed can be coupled with a non-positive and/or positive lock, i.e. the patient bed being particularly and entrained by this locking and introduceable into the opening.

In a preferred embodiment, the patient bed, i.e. the universally employable patient bed, can be coupled to a movable gurney. As a result, it is not only possible to have the patient successively pass through examinations or treatments of different types without a re-bedding being required, but, also, it is possible to accomplish the movement between the individual examination and treatment stations in a way that is ergonomic for the hospital personnel.

In the initially described combination of a number of examination and/or treatment devices, the aforementioned object is inventively achieved by the patient bearing mechanisms having identical coupling devices for coupling of a patient bed. In a combination that is at least connected organizationally, it is advantageously possible for a patient to successively pass through different examinations and/or different treatments at the different examination and/or treatment devices without having to be removed from the patient bed.

The preferred developments and advantages cited for the installation apply analogously to the combination.

In the installation as well as the combination of the invention, the coupling devices can be fashioned in a known way, for example as a snap-in device, latch device, ratchet device or plug-type device.

DESCRIPTION OF THE DRAWING

The single FIGURE is a schematic illustration of an embodiment of a medical installation for examination and/or treatment of a patient, constructed and operating in accordance with the principles of the present invention.

DESCRIPTION OF THE PREFERRED EMBODIMENTS

The drawing schematically shows an installation 1 for medical examination as an example. The installation 1 has a number of examination devices, namely a computed tomography apparatus 3, a magnetic resonance tomography apparatus 5 and an angiography apparatus 7. The examination devices 3, 5, 7 are arranged in different examination rooms in a hospital. The installation 1 also includes at least one universal patient bed 9 on which a patient 11 can be placed.

Respective patient bearing mechanisms 13, 15 and 17 are allocated to the examination devices 3, 5, 7.

For example, the patient support mechanism 13 of the computed tomography apparatus 3 has a pedestal on which an upper part 19 is displaceably mounted for movement in the direction 18. The upper part 19 is introduceable into an opening 29 in the housing 25 of the computed tomography apparatus 3 in order to be able to scan the patient in the longitudinal direction.

The patient support mechanism 15 of the magnetic resonance tomography apparatus 5 has an upper part 21 (for example, a carriage) that is seated at a housing 27 of the magnetic resonance tomography apparatus so as to be movable in the direction 18. The housing 27 has an opening 31 containing an examination region in which a 3D image of the patient 11 is registered after the patient has been introduced into the opening 31.

The patient support mechanism of the angiography apparatus 7 has a rigid upper part 23.

For universal employability, the patient bed 9 is fashioned such that it can be coupled to each of the patient support mechanisms 13, 15, 17 (explicitly shown only at the computed tomography apparatus 3). To this end, it has a coupling fashioned as pegs 35 at its underside. The pegs 35 engage, when the patient bed 9 is placed on the respective part 19, 21, 23, into coupling devices 37 therein. By actuating a lever (not shown) at the respective upper part 19, 21, 23, the rigid coupling of the patient bed 9 to the upper part 19, 21, 23 can be in turn released. The coupling devices 37 are identical at all upper parts 19, 21, 23, so that the patient bed 9 can be universally employed for all of the illustrated examination devices 3, 5, 7.

The upper parts 19, 21, 23 can be fashioned as patient bed or support plate.

Although modifications and changes may be suggested by those skilled in the art, it is the intention of the inventor to embody within the patent warranted hereon all changes and modifications as reasonably and properly come within the scope of his contribution to the art.

We claim:

1. An installation for conducting at least one of a medical examination and a medical treatment of a patient, comprising:
   a plurality of medical devices of different types, selected from the group consisting of medical examination devices and medical treatment devices, disposed at a common installation location;
   a plurality of patient support mechanisms respectively individually, stationarily allocated to said medical devices; and
   a patient bed moveable among and respectively couplable to each of said patient support mechanisms.

2. An installation as claimed in claim 1 wherein each of said support mechanism has a coupling device for releasably fastening said patient bed thereto.

3. An installation as claimed in claim 2 wherein the respective coupling devices of the support mechanisms are identical.

4. An installation as claimed in claim 1 wherein, when said bed is respectively coupled to one of said support mechanism, said bed is upwardly removable from that support mechanism.

5. An installation as claimed in claim 1 wherein, said bed is respectively coupled to one of said support mechanisms, the bed is removable toward a side of that support mechanism.

6. An installation as claimed in claim 1 wherein said support mechanism, when said patient bed is coupled thereto, allows movement of said patient bed on said support mechanism into and out of the medical device to which the support mechanism is allocated.

7. An installation as claimed in claim 1 wherein said patient bed further comprises a coupling adapted to couple said patient bed to a gurney.

8. An installation as claimed in claim 1 wherein one of said medical devices is a magnetic resonance tomography apparatus.

9. An installation as claimed in claim 1 wherein one of said medical devices is a computed tomography apparatus.

10. An installation as claimed in claim 1 wherein one of said medical devices is an angiography device.

11. A medical facility comprising:
    a plurality of medical devices of different types respectively separately located relative to each other, said medical devices being selected from the group consisting of medical examination devices and medical treatment devices;
    a plurality of patient support mechanisms respectively individually, stationarily allocated to said medical devices; and
    each of said patient support mechanisms having a coupling device adapted to couple a patient bed to that patient support mechanism, with the respective coupling devices being identical.

* * * * *